(12) United States Patent
Kaneko et al.

(10) Patent No.: US 9,176,239 B2
(45) Date of Patent: Nov. 3, 2015

(54) RADIOLOGICAL IMAGE CONVERSION PANEL, METHOD OF MANUFACTURING THE SAME, AND RADIOLOGICAL IMAGE DETECTION APPARATUS

(71) Applicant: FUJIFILM Corporation, Tokyo (JP)

(72) Inventors: Yasuhisa Kaneko, Kanagawa (JP); Haruyasu Nakatsugawa, Kanagawa (JP); Keiichirou Sato, Kanagawa (JP); Makoto Kitada, Kanagawa (JP); Kei Miura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/927,529

(22) Filed: Jun. 26, 2013

(65) Prior Publication Data

US 2013/0284934 A1  Oct. 31, 2013

Related U.S. Application Data

(63) Continuation of application No. PCT/JP2011/062403, filed on May 30, 2011.

(30) Foreign Application Priority Data

Dec. 27, 2010  (JP) ................................. 2010-291390

(51) Int. Cl.
*G01J 1/58*  (2006.01)
*G01T 1/20*  (2006.01)
(Continued)

(52) U.S. Cl.
CPC ............... *G01T 1/202* (2013.01); *A61B 6/4216* (2013.01); *B05D 5/06* (2013.01); *G21K 4/00* (2013.01); *G21K 2004/06* (2013.01)

(58) Field of Classification Search
CPC ........ A61B 6/4216; G01T 1/202; G21K 4/00; G21K 4/06; B05D 5/06
USPC ..................... 250/484.4, 483.1, 486.1, 370.11
See application file for complete search history.

(56) References Cited

U.S. PATENT DOCUMENTS 3,481,733 A * 12/1969 Evans .............................. 430/28
3,838,273 A *  9/1974 Cusano ................... 250/214 VT
(Continued)

FOREIGN PATENT DOCUMENTS

CN         101542635 A    9/2009
JP          57-007051 A    1/1982
(Continued)

OTHER PUBLICATIONS

Office Action, dated Aug. 20, 2013, issued by the Japanese Patent Office, in counterpart application No. 2010291390.
(Continued)

*Primary Examiner* — Yara B Green
(74) *Attorney, Agent, or Firm* — Sughrue Mion, PLLC

(57) ABSTRACT

A radiological image conversion panel 2 is provided with a phosphor 18 containing a fluorescent material that emits fluorescence by radiation exposure, in which the phosphor includes, a columnar section 34 formed by a group of columnar crystals which are obtained through columnar growth of crystals of the fluorescent material, and a non-columnar section 36, the columnar section and the non-columnar section are integrally formed to overlap in a crystal growth direction of the columnar crystals, and a thickness of the non-columnar section along the crystal growth direction is non-uniform in a region of at least a part of the non-columnar section.

16 Claims, 7 Drawing Sheets

(51) Int. Cl.
   *G01T 1/202*   (2006.01)
   *A61B 6/00*   (2006.01)
   *G21K 4/00*   (2006.01)
   *B05D 5/06*   (2006.01)

(56) References Cited

U.S. PATENT DOCUMENTS

| | | | | |
|---|---|---|---|---|
| 4,316,092 A * | 2/1982 | Rabatin | ....................... | 250/483.1 |
| 4,437,011 A * | 3/1984 | Noji et al. | ................... | 250/486.1 |
| 4,472,635 A * | 9/1984 | Yokota et al. | ............... | 250/486.1 |
| 4,769,549 A * | 9/1988 | Tsuchino et al. | ........... | 250/484.4 |
| 4,835,396 A * | 5/1989 | Kitada et al. | ................ | 250/483.1 |
| 5,098,818 A * | 3/1992 | Ito et al. | ........................ | 430/434 |
| 5,981,959 A * | 11/1999 | Apte | .......................... | 250/483.1 |
| 6,974,959 B1 * | 12/2005 | Thoms | ........................ | 250/484.4 |
| 7,002,155 B2 * | 2/2006 | Miyata et al. | ............. | 250/370.11 |
| 2005/0051736 A1 | 3/2005 | Isoda et al. | | |
| 2005/0077479 A1 | 4/2005 | Isoda et al. | | |
| 2007/0205380 A1 * | 9/2007 | Isoda | .......................... | 250/484.4 |
| 2009/0078887 A1 | 3/2009 | Yanagita et al. | | |
| 2010/0006762 A1 | 1/2010 | Yoshida et al. | | |
| 2011/0248186 A1 | 10/2011 | Kasai et al. | | |

FOREIGN PATENT DOCUMENTS

| | | |
|---|---|---|
| JP | 06230198 A | 8/1994 |
| JP | 2001330677 A | 11/2001 |
| JP | 3333278 B | 10/2002 |
| JP | 2005069991 A | 3/2005 |
| JP | 200591222 A | 4/2005 |
| JP | 2007315866 A | 12/2007 |
| JP | 2008-088531 A | 4/2008 |
| JP | 2008-111789 A | 5/2008 |
| JP | 2010-185882 A | 8/2010 |
| WO | 2006109460 A1 | 10/2006 |
| WO | 2010061727 A1 | 6/2010 |

OTHER PUBLICATIONS

Written Opinion (PCT/ISA/237), dated Aug. 16, 2010, issued by the International Searching Authority, in counterpart application No. PCT/JP2011/062403.

Office Action issued by the Japan Patent Office dated Feb. 3, 2015, in counterpart Japanese Application No. 2014-091204.

Office Action from the State Intellectual Property Office of P.R. China dated Mar. 24, 2015 in counterpart Chinese Application No. 201180063084.8.

* cited by examiner

RADIOLOGICAL IMAGE CONVERSION PANEL, METHOD OF MANUFACTURING THE SAME, AND RADIOLOGICAL IMAGE DETECTION APPARATUS

CROSS REFERENCE TO RELATED APPLICATION

This is a continuation of International Application No. PCT/JP2011/062403 filed on May 30, 2011, and claims priority from Japanese Patent Application No. 2010-291390, filed on Dec. 27, 2010, the entire disclosures of which are incorporated herein by reference.

TECHNICAL FIELD

The present invention relates to a radiological image conversion panel, a manufacturing method of the radiological image conversion panel and a radiological image detection apparatus provided with the radiological image conversion panel.

BACKGROUND ART

A radiological image detection apparatus using a Flat Panel Detector (FPD) that detects a radiological image to generate digital image data has recently been used practically. The radiological image detection apparatus may immediately confirm an image, as compared to a conventional imaging plate, and thus has been rapidly distributed. There are various types of radiological image detection apparatus, and as one of them, an indirect conversion type of the device is known.

The indirect conversion type of radiological image detection apparatus is provided with a radiological image conversion panel and a sensor panel having two-dimensionally arranged photoelectric conversion elements, in which the radiological image conversion panel has a scintillator formed of a fluorescent material that emits fluorescence through radiation exposure, such as CsI or GOS($Gd_2O_2S$). Typically, the radiological image conversion panel and the sensor panel are bonded so that the scintillator is in close contact with the two-dimensional arrangement of the photoelectric, conversion elements. Radiation passing through the subject is first converted into light by the scintillator of the radiological image conversion panel, and the fluorescence of the scintillator is photoelectrically converted by a group of the photoelectric conversion elements of the sensor panel to generate an electrical signal (digital image data).

As for the indirect conversion type of the radiological image detection apparatus, there has been suggested a radiological image detection apparatus of a so-called surface reading type (ISS: Irradiation Side Sampling) where radiation is allowed to be incident from the sensor panel side (for example, see Patent Literatures 1 and 2). According to the radiological image detection apparatus, the amount of fluorescence emitted from the scintillator in the vicinity of the sensor panel is increased, thereby improving the sensitivity. This may reduce the exposure amount required for detecting a radiological image, thereby reducing the exposure dose of the subject.

Also, there is known a technology of forming a scintillator by a group of columnar crystals through a vapor deposition method so as to improve the sensitivity, in which the columnar crystals are obtained through columnar growth of crystals of a fluorescent material such as CsI on a support (for example, see Patent Literature 3). The columnar crystals formed by the vapor deposition method do not include impurities such as a binding agent, and also has a light guide effect of guiding the fluorescence emitted therefrom in the growth direction of the crystals, thereby suppressing the diffusion of the fluorescence. Accordingly, the improvement in the sensitivity of a radiological image detection apparatus and the sharpness of an image may be achieved.

Further, in order to improve the characteristics of a radiological image conversion panel provided with a scintillator including a group of columnar crystals, various suggestions have been made. For example, in the radiological image conversion panel described in Patent Literature 3, a non-columnar section including a group of spherical crystals of a fluorescent material is formed at the support side of the scintillator, and thereon, a columnar section including a group of columnar crystals is formed. Since the non-columnar section is interposed between the support and the columnar section, the improvement in the adhesion of the scintillator with the support is achieved. Also, by the light reflection in the non-columnar section, the improvement of use efficiency of fluorescence, and thereby the improvement of the sensitivity may be achieved.

CITATION LIST

Patent Literature

Patent Literature 1: JP-B-3333278
Patent Literature 2: JP-A-2001-330677
Patent Literature 3: JP-A-2005-69991

SUMMARY OF INVENTION

Technical Problem

From the viewpoint of light reflection in a non-columnar section, crystals constituting the non-columnar section may preferably have a small diameter cross-section, and a spherical shape. However, many of the crystals constituting the non-columnar section may aggregate with neighboring crystals, so as to form indeterminate aggregates. Accordingly, many of the crystals that constitute the non-columnar section (or include a non-crystalline part) may be partially fused to each other, not only in the thickness direction, but also in the in-plane direction. Each of columnar crystals constituting a columnar section grows with respect to a nucleus of a part of such an indeterminate aggregate. In such a case, columnar crystals with a relatively smaller diameter grow at the initial growth. Then, as the growth proceeds, a plurality of neighboring columnar crystals aggregate with each other, thereby forming one columnar crystal with a large diameter. The junction portion of the columnar section with the non-columnar section has bristled columnar crystals with a relatively small diameter which causes many gaps therebetween, and is very weak against a stress acted by shock, especially, a shear force.

Especially, the scintillator described in Patent Literature 3 is a cumulative phosphor, and a computed radiography (CR) cassette as one example of a radiological image detection apparatus using such a scintillator is relatively light. However, as one example of a radiological image detection apparatus using an FPD, a Digital Radiography (DR) cassette is generally mounted with various electronic components such as a TFT substrate or a driving circuit, and thus is relatively heavy, and its drop shock is higher than the CR cassette. Accordingly, the protection of the scintillator becomes important.

The present invention has been made in consideration of the above described problems and its object is to improve the strength of a radiological image conversion panel.

Solution to Problem (1) It is a radiological image conversion panel provided with a phosphor containing a fluorescent material that emits fluorescence by radiation exposure, in which the phosphor comprises, a columnar section formed by a group of columnar crystals which are obtained through columnar growth of crystals of a fluorescent material, and a non-columnar section, the columnar section and the non-columnar section are integrally formed to overlap in a crystal growth direction of the columnar crystals, and a thickness of the non-columnar section along the crystal growth direction is non-uniform in a region of at least a part of the non-columnar section.

(2) It is a method of manufacturing the radiological image conversion panel of (1), in which the non-columnar section and the columnar section are formed in this order on a support by depositing crystals of the fluorescent material on the support by a vapor deposition method, in which when the non-columnar section is formed, the crystals of the fluorescent material are deposited on the support by varying a degree of vacuum.

(3) It is a radiological image detection apparatus provided with the radiological image conversion panel of (1), and a sensor panel which detects fluorescence generated from the radiological image conversion panel and converts the fluorescence into an electrical signal.

Advantageous Effects of Invention

According to the present invention, in a region of at least a part of the non-columnar section, the thickness is non-uniform, and the junction portion between the columnar section and the non-columnar section is uneven in the plane direction. Accordingly, the resistance against stress such as a shear force may be improved, thereby improving the strength of the radiological image conversion panel.

DESCRIPTION OF EMBODIMENTS

Figure 1:
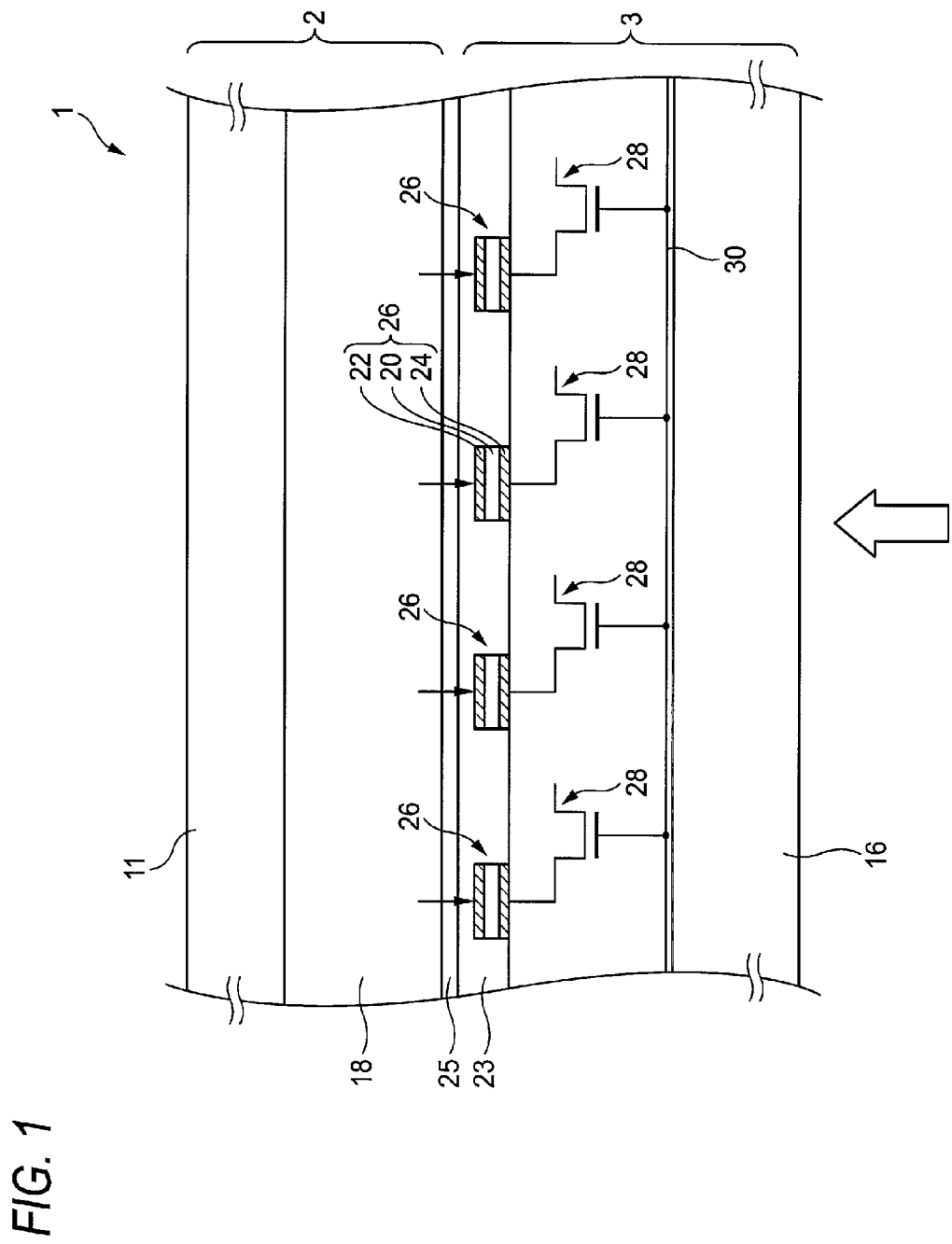
FIG. 1 is a view schematically illustrating a configuration of a radiological image detection apparatus according to one exemplary embodiment of the present invention.
Figure 2:
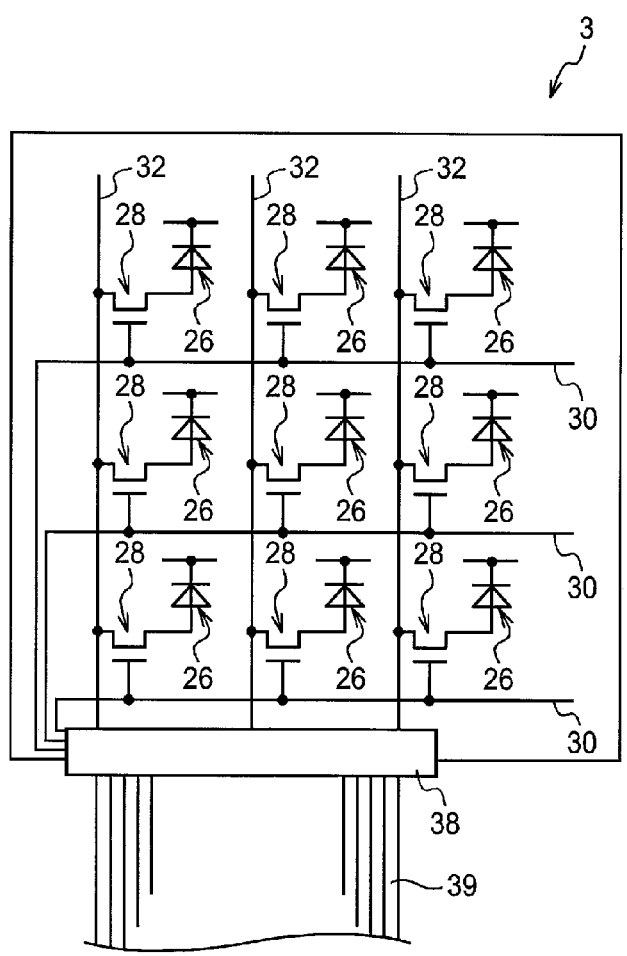
FIG. 2 is a view schematically illustrating a configuration of a sensor panel of the radiological image detection apparatus of FIG. 1.

FIG. 1 illustrates a configuration of a radiological image detection apparatus according to one exemplary embodiment of the present invention, and FIG. 2 illustrates a configuration of a sensor panel of the radiological image detection apparatus of FIG. 1.

A radiological image detection apparatus 1 is provided with a radiological image conversion panel 2 that includes a scintillator 18 (phosphor) that emits fluorescence by radiation exposure, and a sensor panel 3 that includes two dimensional arrangement of photoelectric conversion elements 26 which photoelectrically convert the fluorescence of the scintillator 18 of the radiological image conversion panel 2.

The radiological image conversion panel 2 includes a support 11 on which the scintillator 18 is formed. The radiological image conversion panel 2 is configured separately from the sensor panel 3, and is bonded to the sensor panel 3 via a resin layer, in which the resin layer allows the scintillator 18 to be optically coupled to the photoelectric conversion elements 26 while the surface of the scintillator 18 at the opposite side to the support 11 faces the two-dimensional arrangement of the photoelectric conversion elements 26 of the sensor panel 3.

In the present exemplary embodiment, radiation is irradiated from the sensor panel 3 side, transmitted through the sensor panel 3, and incident on the scintillator 18. The scintillator 18 on which the radiation is incident generates fluorescence, and the generated fluorescence is photoelectrically converted by the photoelectric conversion elements 26 of the sensor panel 3. In the radiological image detection apparatus 1 as configured above, the radiation entrance side of the scintillator 18, which generates a lot of fluorescence, is provided adjacent to the photoelectric conversion elements 26, thereby improving the sensitivity.

The sensor panel 3 has a TFT substrate 16 that includes switching elements 28 formed by Thin Film Transistors (TFTs) on an insulating substrate, and the two-dimensional arrangement of the photoelectric conversion elements 26 is formed on the TFT substrate 16. On the TFT substrate 16, a flattening layer 23 configured to cover the photoelectric conversion elements 26 and flatten the surface of the TFT substrate 16 is formed. An adhesive layer 25 configured to bond the radiological image conversion panel 2 to the sensor panel 3 is formed on the flattening layer 23. The flattening layer 23 and the adhesive layer 25 constitute the above described resin layer. Also, as the resin layer, a matching oil or the like made of transparent liquid or gel may be used. The thickness of the resin layer is preferably 50 μm or less, and more preferably 5 μm to 30 μm from the viewpoints of the sensitivity and the image sharpness.

Each of the photoelectric conversion elements 26 has a configuration where a photoconductive layer 20 that generates electric charges by fluorescence incident from the scintillator 18, and a pair of electrodes provided at the top and bottom surfaces of the photoconductive layer 20. An electrode 22 provided at the surface of the photoconductive layer 20 at the side of the scintillator 18 is a bias electrode that applies a bias voltage to the photoconductive layer 20, and an electrode 24 provided at the opposite side surface is an electric charge collecting electrode that collects the electric charges generated from the photoconductive layer 20.

The switching elements 28 are two-dimensionally arranged on the TFT substrate 16 correspondingly to the two-dimensional arrangement of the photoelectric conversion elements 26, and the electric charge collecting electrodes 24 of the photoelectric conversion elements 26 are connected to the corresponding switching elements 28 of the TFT substrate 16. The electric charges collected by the electric charge collecting electrodes 24 are read out by the switching elements 28.

On the TFT substrate 16, a plurality of gate lines 30 are provided extending in one direction (row direction) to set each of the switching elements 28 to be ON/OFF, and a plurality of signal lines (data lines) 32 are provided extending in a direction (column direction) perpendicular to the gate lines 30 to read out the electric charges via the switching elements 28 in the ON state. Then, in the periphery of the TFT substrate 16, a connection terminal 38 connected to the gate lines 30 and the signal lines 32, respectively, is provided. The connection terminal 38, as illustrated in FIG. 2, is connected to a circuit board (not illustrated) via a connection circuit 39. The circuit board includes a gate line driver as an external circuit, and a circuit processing unit.

The switching elements 28 are sequentially placed in the ON state line by line by the signal supplied via the gate lines 30 from the gate line driver. Then, the electric charges read out by the switching elements 28 placed in the ON state are transmitted as electric charge signals via the signal lines 32, and input to the signal processing unit. Accordingly, the electric charges are sequentially read out line by line, and converted into electrical signals in the signal processing unit, to generate digital image data.

Hereinafter, the radiological image conversion panel 2 and the scintillator 18 thereof will be described in detail.

Figure 3:
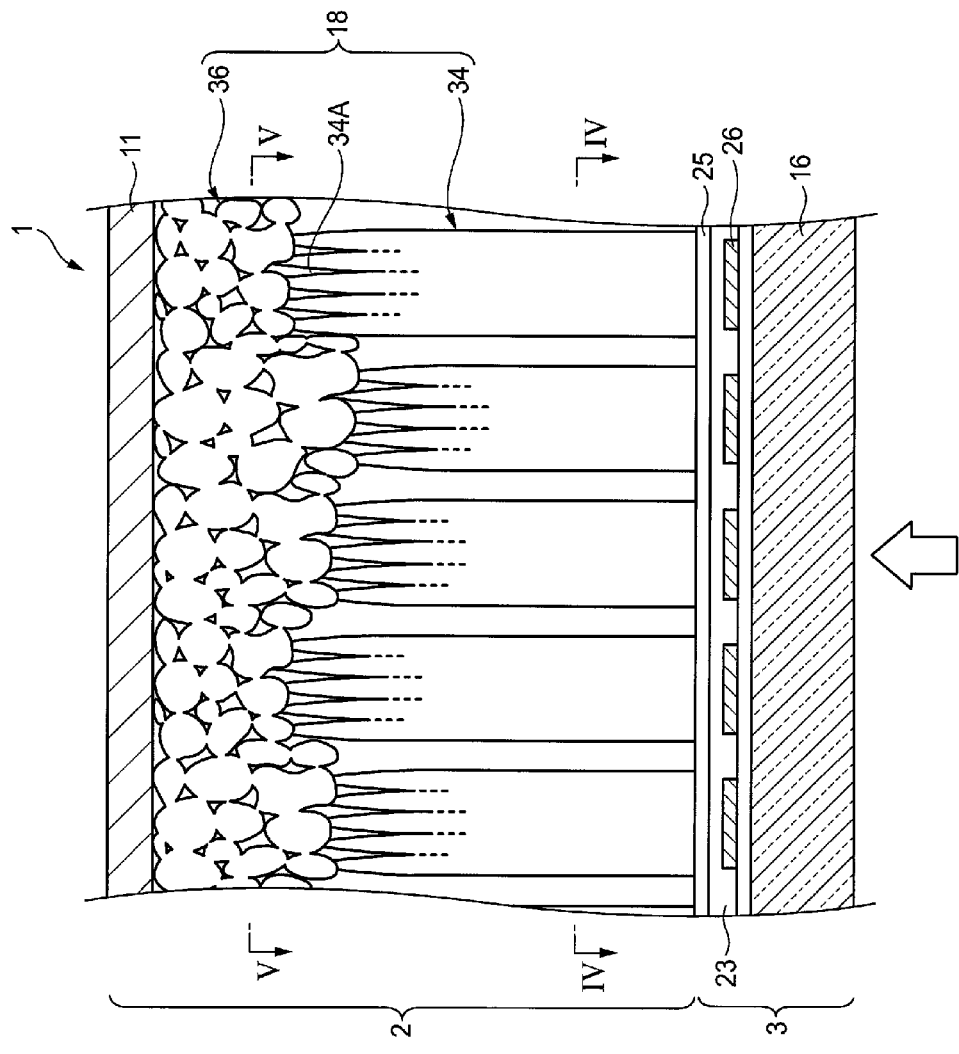
FIG. 3 is a view schematically illustrating a configuration of a radiological image conversion panel of the radiological image detection apparatus of FIG. 1.

FIG. 3 schematically illustrates the configuration of the radiological image conversion panel 2.

The radiological image conversion panel 2 includes the support 11 and the scintillator 18 formed on the support 11.

As for the support 11, a carbon plate, a carbon fiber reinforced plastic (CFRP), a glass plate, a quartz substrate, a sapphire substrate or a metal sheet selected from iron, tin, chromium, aluminum or the like, may be used. However, the support is not limited to those described above as long as it may allow the scintillator 18 to be formed thereon.

As for the fluorescent material constituting the scintillator 18, for example, CsI:Tl NaI:Tl (thallium-activated sodium iodide), CsI:Na (sodium-activated cesium iodide) or the like may be used. From among these, CsI:Tl is preferable since its emission spectrum is suitable for the maximum value (around 550 nm) of the spectral sensitivity of a-Si photodiode.

The scintillator 18 is configured to include a columnar section 34 provided at the opposite side of the support 11, and a non-columnar section 36 provided at the support 11 side. The columnar section 34 and the non-columnar section 36 are continuously formed to be stacked in layers on the support 11. Although details will be described later, for example, a vapor deposition method may be used for the formation. Also, although the columnar section 34 and the non-columnar section 36 are formed by the same fluorescent material, the addition amount of an activator such as Tl may be varied.

The columnar section 34 is formed by a group of columnar crystals obtained by columnar growth of crystals of the fluorescent material. Also, there is a case where a plurality of neighboring columnar crystals may be bonded to each other so as to form one columnar crystal. There is a gap between adjacent columnar crystals, and thus respective columnar crystals exist independently with each other.

The non-columnar section 36 is formed by a group of spherical crystals obtained by growing crystals of the fluorescent material in a substantially spherical shape with a relatively small diameter. Also, in the non-columnar section 36, a non-crystalline part of the fluorescent material may be included. In the non-columnar section 36 formed by the group of the spherical crystals, the crystals (that may partially include a non-crystalline part) irregularly overlap, and some crystals may be fused to each other in the thickness direction or the in-plane direction. Thus, a clear gap between the crystals hardly occurs.

The radiological image conversion panel 2 is bonded to the sensor panel 3 while the surface of the scintillator 18 at the opposite side to the support 11, that is, the tip of each of the columnar crystals of the columnar section 34, faces the two-dimensional arrangement of the photoelectric conversion elements 26 of the sensor panel 3. Accordingly, at the radiation entrance side of the scintillator 18, the columnar section 34 including the group of the columnar crystals is disposed.

The fluorescence occurring in each of the columnar crystals of the columnar section 34 is suppressed from diffusing since total reflection within the columnar crystal is repeated due to a refractive index difference between the columnar crystal and the gap (air) around the crystal. Then, the fluorescence is guided to the photoelectric conversion element 26 facing the columnar crystal. Accordingly, the sharpness of the image is improved.

The fluorescence which occurs in each of the columnar crystals of the columnar section 34 and is toward the opposite side to the sensor panel 3, that is, the support 11 side, is reflected toward the sensor panel 3 side in the non-columnar section 36. This increases the use efficiency of the fluorescence, thereby improving the sensitivity.

Also, each of the columnar crystals of the columnar section 34 is relatively thin at the initial growth, and becomes thicker according to the crystal growth. At the junction portion 34A of the columnar section 34 with the non-columnar section 36, columnar crystals with a small diameter are bristled, and many relatively large gaps extend in the direction of crystal growth, which increases the porosity. At one side, the non-columnar section 36 is formed by spherical crystals with a small diameter or aggregates thereof, in which individual gaps are relatively small, and are dense as compared to those in the columnar section 34, and thus, the porosity is low. Since the non-columnar section 36 is interposed between the support 11 and the columnar section 34, the adhesion of the scintillator 18 with the support 11 is the improved. Accordingly, the resistance against stress acted by warping or shock due to a linear expansion difference between the support 11 and the TFT substrate 16 of the sensor panel 3 is improved, and the scintillator 18 is suppressed from being peeled off from the support 11.

Figure 4:
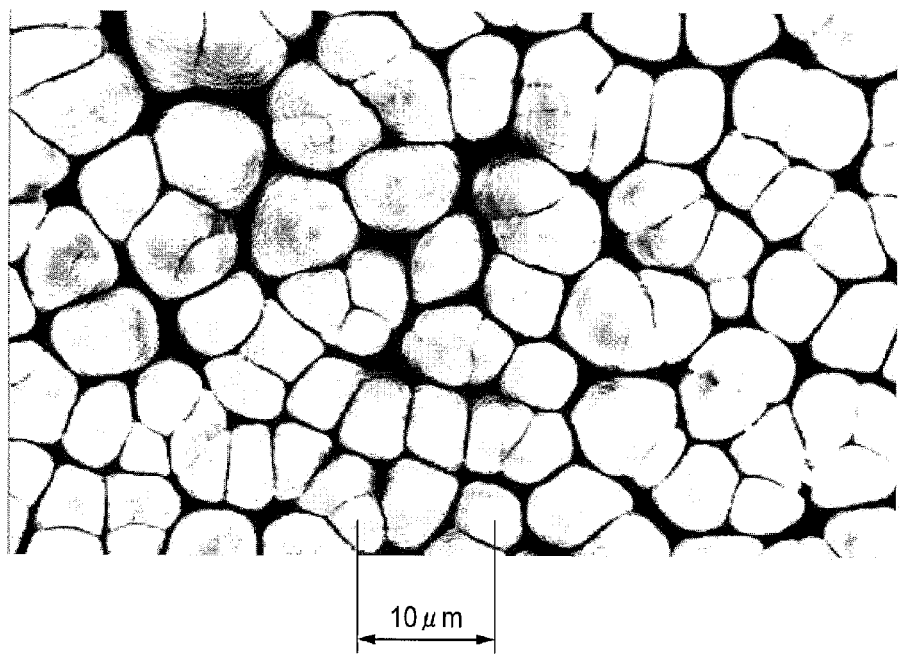
FIG. 4 is a view illustrating a IV-IV cross section of a phosphor of the radiological image conversion panel of FIG. 3.

FIG. 4 is an electron micrograph illustrating a IV-IV cross section of the scintillator 18 of FIG. 3.

As can be clearly seen in FIG. 4, in the columnar section 34, the columnar crystals show a substantially uniform cross sectional diameter in the crystal growth direction, and also the columnar crystals exist independently with each other with gaps around the columnar crystals. The crystal diameter of the columnar crystals is preferably, 2 $\mu$m or more and 8 $\mu$m or less from the viewpoints of a light guide effect, a mechanical strength, and a pixel defect prevention. When the crystal diameter is too small, there is a concern that each of the columnar crystals lacks the mechanical strength, and thus is damaged by shock or the like. When the crystal diameter is too large, the number of the columnar crystals in each of the photoelectric conversion elements 26 is decreased. Thus, there is a concern that when a crack occurs in the crystals, the probability of defect in a corresponding element increases.

Here, the crystal diameter refers to a maximum diameter of a crystal observed from the top surface in the growing direction of the columnar crystal. In a specific measuring method, the columnar diameter (crystal diameter) is measured by observation from a plane perpendicular to the film thickness direction of the columnar crystals with an SEM (scanning electron micrograph). Observation is performed with a magnification (about 2,000×) that allows 100 to 200 columnar crystals 20A to be observed when the scintillator is viewed from the surface at one shot. A value obtained by measuring and taking an average on the maximum values of the columnar diameters of columnar crystals obtained for all the crystals included at the one shot is employed. The columnar diameters (m) are read to two decimal places, and the average value is determined by rounding off to one decimal place in accordance with JIS Z 8401.

Figure 5:
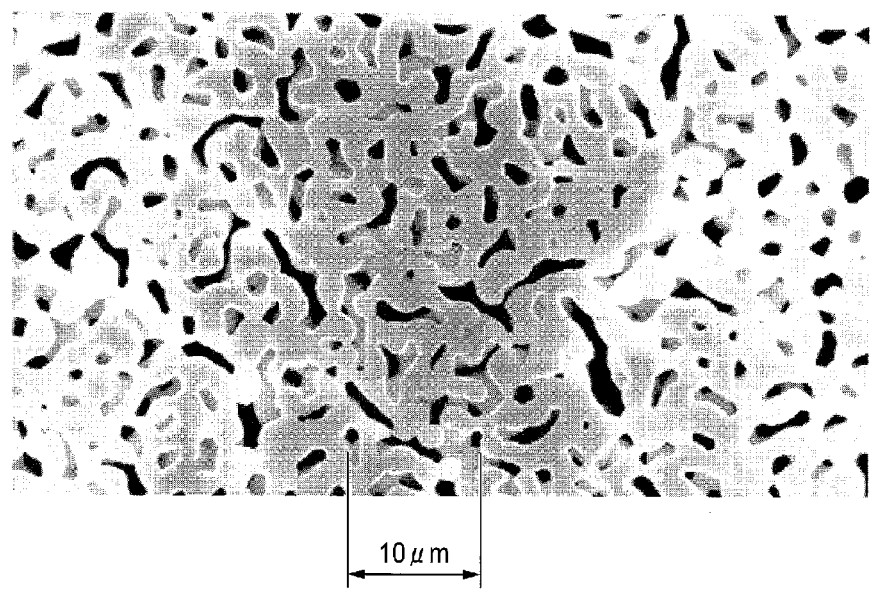
FIG. 5 is a view illustrating a V-V cross section of a phosphor of the radiological image conversion panel of FIG. 3.

FIG. 5 is an electron micrograph illustrating a V-V cross section of the scintillator 18 of FIG. 3.

As can be clearly seen in FIG. 5, in the non-columnar section 36, since the crystals are irregularly bonded to or overlapped each other, a clear gap between the crystals is not confirmed unlike in the columnar section 34. The diameter of the crystals constituting the non-columnar section 36 is preferably 0.5 μm or more and 7.0 μm or less from the viewpoints of an adhesion and a light reflection. When the crystal diameter is too small, there is a concern that the gap gets closer to 0, thereby lowering the light reflection function. When the crystal diameter is too large, there is a concern that the flatness is lowered, thereby lowering the adhesion with the support 11. Also, the shape of the crystals constituting the non-columnar section 36 is preferably substantially spherical from the viewpoint of the light reflection.

Here, in a case where crystals are bonded to each other, the crystal diameter is measured as follows. A line connecting concave portions (recesses) occurring between the adjacent crystals is considered as a boundary between the crystals, and the bonded crystals are separated to be the smallest polygons so that a columnar diameter and a crystal diameter corresponding to the columnar diameter are measured. Then, the average value thereof is determined and is employed in the same manner as the crystal diameter of the columnar section 34.

In the thicknesses of the columnar section 34 and the non-columnar section 36, when the thickness of the columnar section 34 is set as t1, and the thickness of the non-columnar section 36 is set as t2, (t2/t1) is preferably 0.01 or more and 0.25 or less, and more preferably 0.02 or more and 0.1 or less. When (t2/t1) is within the above described range, a fluorescence efficiency, a light diffusion prevention and a light reflection may be placed in a suitable range, thereby improving the sensitivity and the image sharpness.

Also, the thickness t1 of the columnar section 34 depends on the energy of radiation, but is preferably 200 μm or more and 700 μm or less from the viewpoints of a sufficient radiation absorption and an image sharpness in the columnar section 34. When the thickness of the columnar section 34 is too small, there is a concern that radiation may not be sufficiently absorbed, and thus the sensitivity is lowered. When the thickness is too large, there is a concern that the light diffusion occurs, and thus the image sharpness is lowered even by the light guide effect of the columnar crystals.

The thickness t2 of the non-columnar section 36 is preferably 5 μm or more and 125 μm or less from the viewpoints of the adhesion with the support 11, and the light reflection. When the thickness of the non-columnar section 36 is too small, there is a concern that a sufficient adhesion with the support 11 may not be obtained. When the thickness is too large, there is a concern that contribution of fluorescence in the non-columnar section 36, and diffusion by light reflection in the non-columnar section 36 are increased, thereby lowering the image sharpness.

Further, in the present radiological image conversion panel 2, the thickness distribution of the non-columnar section 36 is non-uniform. Since the columnar section 34 and the non-columnar section 36 are continuously formed by crystals of the same fluorescent material, the bonding of the columnar section 34 to the non-columnar section 36 is relatively stronger as compared to the bonding of the columnar section 34 to different materials such as the support 11. However, each of the columnar crystals of the columnar section 34 grows with respect to a nucleus of a relatively small spherical crystal of the non-columnar section 36, and is relatively thin at the initial growth, and becomes thicker according to the crystal growth. At the junction portion 34A of the columnar section 34 with the non-columnar section 36, columnar crystals with a small diameter are bristled, and relatively large gaps extend in the direction of crystal growth. Further, although each of the columnar crystals becomes thick according to the growth, and a plurality of neighboring columnar crystals are in contact with each other, these crystals are not always bonded (fused) to each other. Accordingly, there is a concern that the junction portion 34A of the columnar section 34 may lack resistance against stress acted by shock or the like. Accordingly, the non-columnar section 36 has non-uniform thickness distribution, thereby compensating the stress resistance at the junction portion 34A.

Due to the non-uniform thickness distribution of the non-columnar section 36, the junction portion 34A becomes uneven in the plane direction. In each of the columnar crystals growing at the thin thickness region of the non-columnar section 36, the junction portion 34A is surrounded by a dense non-columnar section 36 in the neighborhood thereof. The junction portion 34A of each of the columnar crystals growing at the thick thickness region of the non-columnar section 36 is surrounded by neighboring columnar crystals of which the growth proceeds at the thin thick region of the non-columnar section 36 and the diameter becomes large. Accordingly, the resistance against stress such as a shear force may be increased, thereby improving the strength.

The thickness of each portion of the non-columnar section 36 is preferably distributed within the above described range of 5 μm or more and 125 μm or less from the viewpoints of the adhesion with the support 11 and the light reflection. Also, in the present radiological image conversion panel 2, the non-columnar section 36 has a constantly non-uniform thickness distribution throughout. However, when the non-columnar section 36 is divided into a plurality of regions, non-uniformity (difference between the maximum thickness and the minimum thickness, or deviation in the thickness distribution) may be different in respective regions.

Hereinafter, the method of preparing the above described scintillator 18 will be exemplarily descried.

The scintillator 18 is preferably directly formed on the surface of the support 11 by a vapor deposition method. In the vapor deposition method, the non-columnar section 36 and the columnar section 34 may be in this order sequentially integrally formed. Hereinafter, a case of using CsI:Tl as the fluorescent material is exemplarily described.

The vapor deposition method may be performed according to a conventional method. Under the environment of degree of vacuum 0.01 Pa to 10 Pa, CsI:Tl is heated and vaporized, for example, by means of applying electric current to a resistance heating-type crucible, and then the temperature of the support 11 is adjusted to room temperature (20° C.) to 300° C. so as to deposit CsI:Tl on the support.

When the crystalline phase of CsI:Tl is formed on the support 11 by the vapor deposition method, at the initial stage, spherical crystals with a relatively small diameter or aggregates thereof are formed. Then, by varying at least one condition of the degree of vacuum, and the temperature of the support 11, it is possible to form the columnar section 34 in succession to the formation of the non-columnar section 36. That is, after the spherical crystals are deposited to a predetermined thickness, the columnar crystals may be grown by increasing the degree of vacuum, and/or increasing the temperature of the support 11.

Then, in the step of forming the non-columnar section 36, deposition with variation of the degree of vacuum imparts non-uniform thickness distribution to the non-columnar section 36. When the degree of vacuum is varied, the melt state of CsI:Tl is changed. Then, a time is required until the melt state is stabilized. While the melt state is unstable, the deposition may be continuously performed, thereby imparting non-uniform thickness distribution to the non-columnar section 36.

The scintillator 18 may be efficiently and easily prepared in the manner as described above. Also, according to the preparation method, there is an advantage in that the scintillator with various specifications may be simply prepared in accordance with designs by controlling the degree of vacuum or the support temperature in the film formation of the scintillator 18.

As described above, in the radiological image conversion panel 2 and the radiological image detection apparatus 1 including the same, the thickness of the non-columnar section 36 of the scintillator 18 is non-uniform, and the junction portion 34A of the columnar section 34 with the non-columnar section 36 is uneven in the plane direction. Accordingly, the resistance against stress such as a shear force may be improved, thereby improving the strength of the radiological image conversion panel 2.

Also, although in the above described radiological image detection apparatus 1, radiation is incident from the sensor panel 3 side, a configuration where radiation is incident from the radiological image conversion panel 2 side may be employed.

Also, although in the above described radiological image detection apparatus 1, the radiological image conversion panel 2 and the sensor panel 3 are bonded via the flattening layer 23 and the adhesive layer 25, there is no particular limitation in the bonding method between the radiological image conversion panel 2 and the sensor panel 3. The scintillator 18 of the radiological image conversion panel 2 and the arrangement of the photoelectric conversion elements 26 of the sensor panel 3 may be optically coupled, or a method of directly bringing the scintillator 18 in close contact with the arrangement of the photoelectric conversion elements 26 may be employed. In this case, it is not necessary that the surfaces of the two elements are in completely close contact with each other. Even though an unevenness exists on the surface of the scintillator 18, the two elements may be optically coupled while disposed in the overlapping state. When the fluorescence occurring in the scintillator 18 is incident on the arrangement of the photoelectric conversion elements 26, the effect of the present invention may be achieved.

Figure 6:
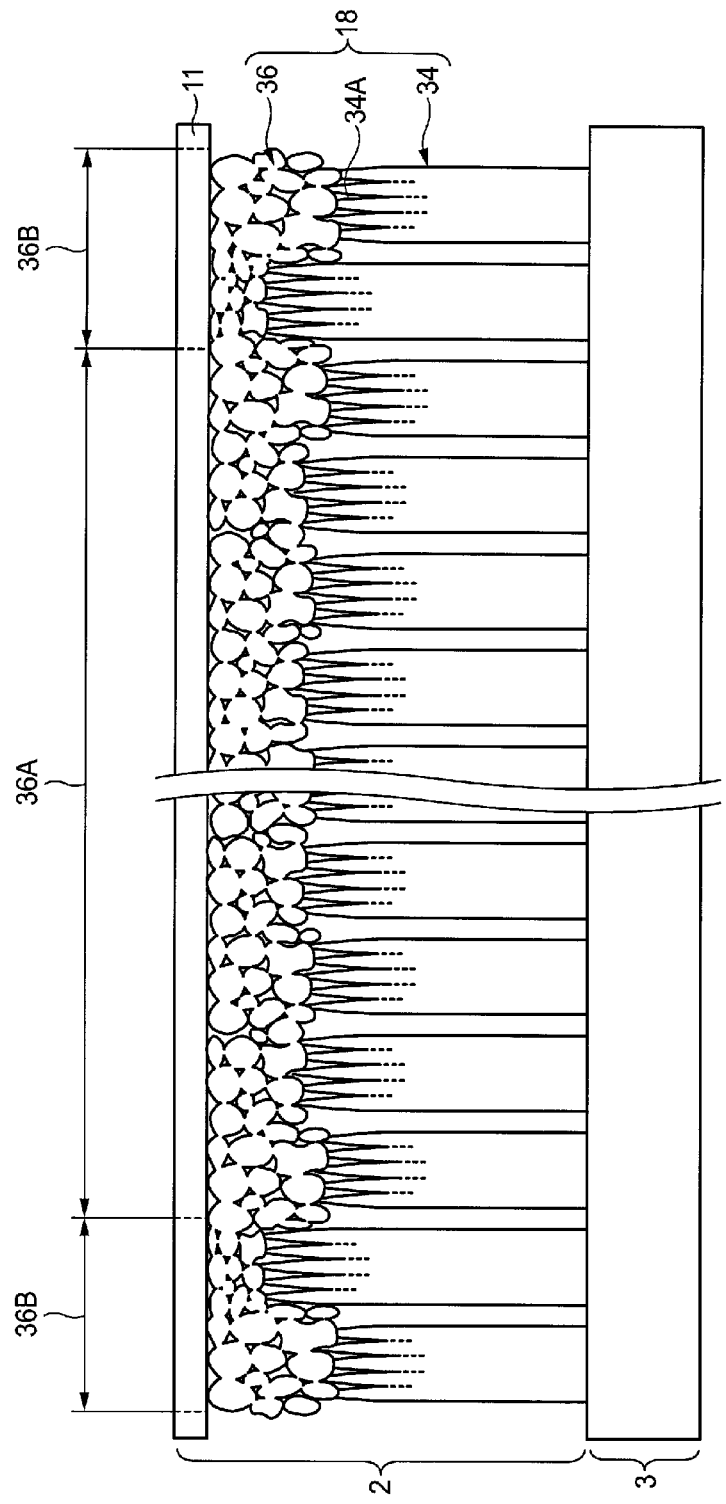
FIG. 6 is a view schematically illustrating a modified example of the radiological image conversion panel of FIG. 3.

FIG. 6 illustrates a modified example of the above described radiological image conversion panel 2.

In the present modified example, although the non-columnar section 36 has a non-uniform thickness distribution throughout, a difference between the maximum thickness and the minimum thickness in a central region 36A is set to be less than a difference between the maximum thickness and the minimum thickness in a peripheral region 36B. That is, the deviation in the thickness distribution in the central region 36A is set to be less than that in the thickness distribution in the peripheral region 36B.

The scintillator 18 is formed in a size equal to or greater than the two-dimensional arrangement of the photoelectric conversion elements 26 so as to cover the two-dimensional arrangement of the photoelectric conversion elements 26. Meanwhile, in the two-dimensional arrangement of the photoelectric conversion elements 26, elements in a central region (effective imaging region) are generally used for detecting a radiological image because noise may be easily superimposed on elements in a peripheral region. For this reason, the central region of the scintillator 18, which overlaps the above described effective imaging region, mainly contributes to the detection of the radiological image. The contribution by the peripheral region excluding the effective imaging region is relatively low.

The non-columnar section 36 of the scintillator 18 has a light reflection function as described above, and the non-uniformity in the thickness of the non-columnar section 36 may induce non-uniformity in light reflection. Therefore, by reducing the difference between the maximum thickness and the minimum thickness in the central regions 36A of the non-columnar section 36 overlapping the above described effective imaging region, the non-uniformity of light reflection in the corresponding region may be reduced, thereby lowering the shock on the image.

Meanwhile, in the peripheral region 36B of the non-columnar section 36, the contribution to the detection of the radiological image is relatively low as described above, and thus, even though the difference between the maximum thickness and the minimum thickness is set to be large, there is no specific problem. Also, the peripheral region of the scintillator 18 is susceptible to stress caused by warping or shock. Therefore, when the difference between the maximum thickness and the minimum thickness in the peripheral region 36B of the non-columnar section 36 is set to be large, it is possible to secure the resistance against the stress acted on the junction portion between the columnar section 34 and the non-columnar section 36.

Further, the thickness distribution in the central region 36A of the non-columnar section 36 may be uniform, which may uniformize the light reflection in the central region 34A, thereby further reducing the shock on the detected image. Also, the uniform thickness distribution indicates that the difference between that the maximum thickness and the minimum thickness is less than 5 µm.

The scintillator 18 which has a small deviation in the thickness distribution or a uniform thickness distribution in the central region 36A of the non-columnar section 36 may be prepared by depositing the crystals of CsI:Tl with variation of the degree of vacuum, and during at least a part of the period for variation of the degree of vacuum, further covering the center of an opening of a crucible containing a melt of CsI:Tl with a shutter, in the step of forming the non-columnar section 36. As described above, the melt state of CsI:Tl is varied as the degree of vacuum is varied. While the melt state is unstable, deposition may be continuously performed, thereby imparting a non-uniform thickness distribution. At this time, when the center of the opening of the crucible corresponding to the central region 36A of the non-columnar section 36 is covered with the shutter, crystals may be hardly deposited in the central region 36A. As a result, the deviation in the thickness distribution in the central region 36A is reduced or the thickness distribution becomes uniform.

Figure 7:
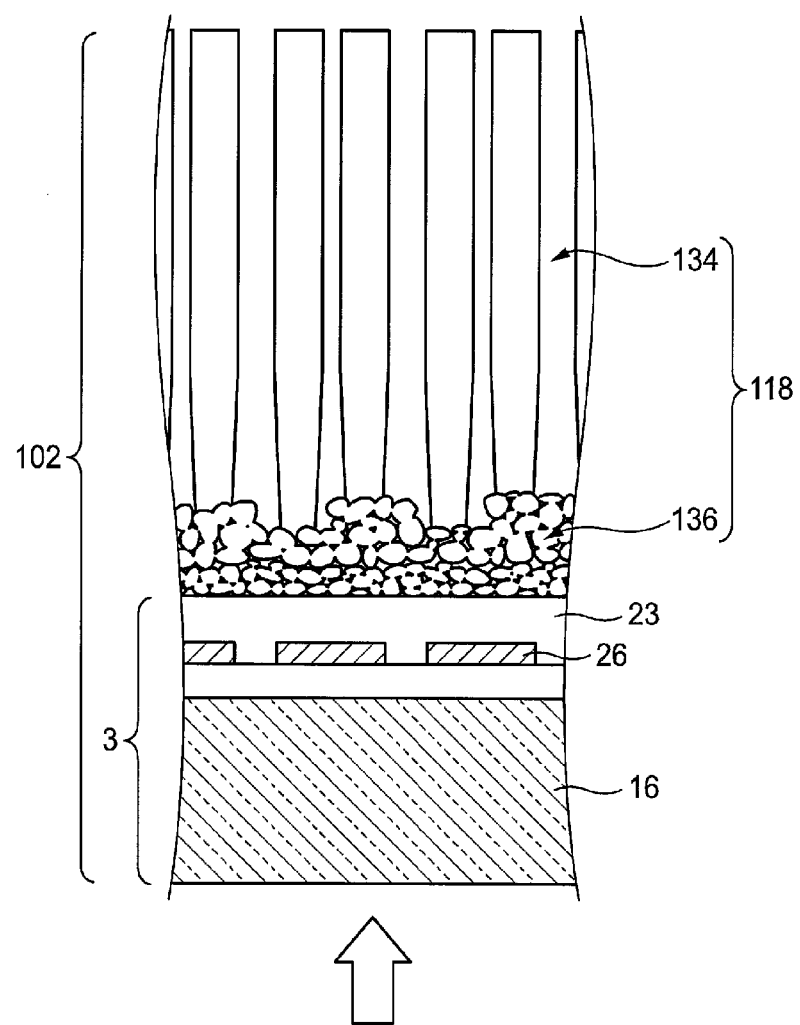
FIG. 7 is a view schematically illustrating a configuration of a radiological image detection apparatus according to another exemplary embodiment of the present invention.

FIG. 7 is a view illustrating a radiological image detection apparatus according to another exemplary embodiment of the present invention. Further, the same components as those in the above described radiological image detection apparatus 1 will be denoted by the same reference numerals, and their description will be omitted or simplified.

In a radiological image detection apparatus 101 illustrated in FIG. 7, a scintillator 118 of a radiological image conversion panel 102 is directly formed on the surface of a sensor panel 3 provided with a two-dimensional arrangement of photoelectric conversion elements 26. That is, as a support of the scintillator 118, the sensor panel 3 is used.

The scintillator 118 includes a columnar section 134 and a non-columnar section 136, and on the surface of the sensor panel 3, the non-columnar section 136 and the columnar section 134 are sequentially continuously formed to be stacked in layers. Since between the sensor panel 3 and the columnar section 134, the non-columnar section 136 is interposed, the adhesion of the scintillator 118 with the sensor panel 3 is improved, and thus the scintillator 118 is suppressed from being peeled off from the sensor panel 3. The non-columnar section 136 has a non-uniform thickness distribution, and thus the resistance against stress such as a shear force acted on a junction portion between the columnar section 134 and the non-columnar section 136 is improved, thereby improving the strength. The columnar section 134 and the non-columnar section 136 may be formed on the surface of the sensor panel 3 by the above described vapor deposition method.

Also, in the present radiological image detection apparatus 101, between the columnar section 134 of the scintillator 118 and the two-dimensional arrangement of the photoelectric conversion elements 26 of the sensor panel 3, the non-columnar section 136 of the scintillator 118 is interposed. In this case, there is a concern that the light reflection in the non-columnar section 136 may suppress the fluorescence occurring in each of columnar crystals of the columnar section 134 from being incident on the corresponding photoelectric conversion element 26. Accordingly, the thickness of the non-columnar section 136 is preferably small within a range allowing the adhesion with the sensor panel 3 to be secured.

Each of the above described radiological image detection apparatus may detect a radiological image with a high sensitivity and a high definition, and thus may be used while embedded within various devices requiring detection of a sharp image at a low radiation irradiation dose, including an X-ray imaging device for medical diagnosis such as mammography. For example, the device has a wide application range thereof because it may be used as an X-ray imaging device for industrial use for a non-destructive test, or as a device for detecting corpuscular beams (α rays, β-rays, γ rays) besides electromagnetic waves.

Hereinafter, materials that may be used for respective components constituting the sensor panel 3 will be described.

[Photoelectric Conversion Element]

Although inorganic semiconductor materials such as amorphous silicon are often used as the photoconductive layers 20 of the aforementioned photoelectric conversion elements 26 (refer to FIG. 1), any OPC (Organic Photoelectric Conversion) material disclosed in JP-A-2009-32854 can be used. A film formed out of the OPC material (hereinafter referred to as OPC film) can be used as the photoconductive layers 20. The OPC film contains an organic photoelectric conversion material, which absorbs light emitted from the scintillator and generates electric charges corresponding to the absorbed light. Thus, the OPC film containing the organic photoelectric conversion material has a sharp absorption spectrum in a visible light range. Electromagnetic waves other than the light emitted by the scintillator are hardly absorbed by the OPC film. Thus, noise generated by radioactive rays such as X-rays absorbed by the OPC film can be suppressed effectively.

It is preferable that the absorption peak wavelength of the organic photoelectric conversion material forming the OPC film is closer to the peak wavelength of light emitted by the scintillator in order to more efficiently absorb the light emitted by the scintillator. Ideally, the absorption peak wavelength of the organic photoelectric conversion material agrees with the peak wavelength of the light emitted by the scintillator. However, if the difference between the absorption peak wavelength of the organic photoelectric conversion material and the peak wavelength of the light emitted by the scintillator is small, the light emitted by the scintillator can be absorbed satisfactorily. Specifically, the difference between the absorption peak wavelength of the organic photoelectric conversion material and the peak wavelength of the light emitted by the scintillator in response to radioactive rays is preferably not larger than 10 nm, more preferably not larger than 5 nm.

Examples of the organic photoelectric conversion material that can satisfy such conditions include arylidene-based organic compounds, quinacridone-based organic compounds, and phthalocyanine-based organic compounds. For example, the absorption peak wavelength of quinacridone in a visible light range is 560 nm. Therefore, when quinacridone is used as the organic photoelectric conversion material and CsI(Tl) is used as the scintillator material, the aforementioned difference in peak wavelength can be set within 5 nm so that the amount of electric charges generated in the OPC film can be increased substantially to the maximum.

At least a part of an organic layer provided between the bias electrode 22 and the charge collection electrode 24 can be formed out of an OPC film. More specifically, the organic layer can be formed out of a stack or a mixture of a portion for absorbing electromagnetic waves, a photoelectric conversion portion, an electron transport portion, an electron hole transport portion, an electron blocking portion, an electron hole blocking portion, a crystallization prevention portion, electrodes, interlayer contact improvement portions, etc.

Preferably the organic layer contains an organic p-type compound or an organic n-type compound. An organic p-type semiconductor (compound) is a donor-type organic semiconductor (compound) as chiefly represented by an electron hole transport organic compound, meaning an organic compound having characteristic to easily donate electrons. More in detail, of two organic materials used in contact with each other, one with lower ionization potential is called the donor-type organic compound. Therefore, any organic compound may be used as the donor-type organic compound as long as the organic compound having characteristic to donate electrons. Examples of the donor-type organic compound that can be used include a triarylamine compound, a benzidine compound, a pyrazoline compound, a styrylamine compound, a hydrazone compound, a triphenylmethane compound, a carbazole compound, a polysilane compound, a thiophene compound, a phthalocyanine compound, a cyanine compound, a merocyanine compound, an oxonol compound, a polyamine compound, an indole compound, a pyrrole compound, a pyrazole compound, a polyarylene compound, a fused aromatic carbocyclic compound (naphthalene derivative, anthracene derivative, phenanthrene derivative, tetracene derivative, pyrene derivative, perylene derivative, fluoranthene derivative), a metal complex having a nitrogen-containing heterocyclic compound as a ligand, etc. The donor-type organic semiconductor is not limited thereto but any organic compound having lower ionization potential than the organic compound used as an n-type (acceptor-type) compound may be used as the donor-type organic semiconductor.

The n-type organic semiconductor (compound) is an acceptor-type organic semiconductor (compound) as chiefly represented by an electron transport organic compound, meaning an organic compound having characteristic to easily accept electrons. More specifically, when two organic compounds are used in contact with each other, one of the two organic compounds with higher electron affinity is the acceptor-type organic compound. Therefore, any organic compound may be used as the acceptor-type organic compound as long as the organic compound having characteristic to accept electrons. Examples thereof include a fused aromatic carbocyclic compound (naphthalene derivative, anthracene derivative, phenanthrene derivative, tetracene derivative, pyrene derivative, perylene derivative, fluoranthene derivative), a 5- to 7-membered heterocyclic compound containing a nitrogen atom, an oxygen atom or a sulfur atom (e.g. pyridine, pyrazine, pyrimidine, pyridazine, triazine, quinoline, quinoxaline, quinazoline, phthalazine, cinnoline, isoquinoline, pteridine, acridine, phenazine, phenanthroline, tetrazole, pyrazole, imidazole, thiazole, oxazole, indazole, benzimidazole, benzotriazole, benzoxazole, benzothiazole, carbazole, purine, triazolopyridazine, triazolopyrimidine, tetrazaindene, oxadiazole, imidazopyridine, pyralidine, pyrrolopyridine, thiadiazolopyridine, dibenzazepine, tribenzazepine etc.), a polyarylene compound, a fluorene compound, a cyclopentadiene compound, a silyl compound, and a metal complex having a nitrogen-containing heterocyclic compound as a ligand. The acceptor-type organic semiconductor is not limited thereto. Any organic compound may be used as the acceptor-type organic semiconductor as long as the organic compound has higher electron affinity than the organic compound used as the donor-type organic compound.

As for p-type organic dye or n-type organic dye, any known dye may be used. Preferred examples thereof include cyanine dyes, styryl dyes, hemicyanine dyes, merocyanine dyes (including zero-methine merocyanine (simple merocyanine)), trinuclear merocyanine dyes, tetranuclear merocyanine dyes, rhodacyanine dyes, complex cyanine dyes, complex merocyanine dyes, alopolar dyes, oxonol dyes, hemioxonol dyes, squarylium dyes, croconium dyes, azamethine dyes, coumarin dyes, arylidene dyes, anthraquinone dyes, triphenylmethane dyes, azo dyes, azomethine dyes, spiro compounds, metallocene dyes, fluorenone dyes, flugide dyes, perylene dyes, phenazine dyes, phenothiazine dyes, quinone dyes, indigo dyes, diphenylmethane dyes, polyene dyes, acridine dyes, acridinone dyes, diphenylamine dyes, quinacridone dyes, quinophthalone dyes, phenoxazine dyes, phthaloperylene dyes, porphyrin dyes, chlorophyll dyes, phthalocyanine dyes, metal complex dyes, and fused aromatic carbocyclic dyes (naphthalene derivative, anthracene derivative, phenanthrene derivative, tetracene derivative, pyrene derivative, perylene derivative, fluoranthene derivative).

A photoelectric conversion film (photosensitive layer) which has a layer of a p-type semiconductor and a layer of an n-type semiconductor between a pair of electrodes and at least one of the p-type semiconductor and the n-type semiconductor is an organic semiconductor and in which a bulk heterojunction structure layer including the p-type semiconductor and the n-type semiconductor is provided as an intermediate layer between those semiconductor layers may be used preferably. The bulk heterojunction structure layer included in the photoelectric conversion film can cover the defect that the carrier diffusion length of the organic layer is short. Thus, the photoelectric conversion efficiency can be improved. The bulk heterojunction structure has been described in detail in JP-A-2005-303266.

It is preferable that the photoelectric conversion film is thicker in view of absorption of light from the phosphor layer. The photoelectric conversion film is preferably not thinner than 30 nm and not thicker than 300 nm, more preferably not thinner than 50 nm and not thicker than 250 nm, particularly more preferably not thinner than 80 nm and not thicker than 200 nm in consideration of the ratio which does make any contribution to separation of electric charges.

As for any other configuration about the aforementioned OPC film, for example, refer to description in JP-A-2009-32854.

[Switching Element]

Although inorganic semiconductor materials such as amorphous silicon are often used as an active layer of the switching elements 28, organic materials may be used, for example, as disclosed in JP-A-2009-212389. Organic TFT may have any type of structure but a field effect transistor (FET) structure is the most preferable. In the FET structure, a gate electrode is provided partially an upper surface of an insulation substrate. An insulator layer is provided to cover the electrode and touch the substrate in the other portion than the electrode. Further, a semiconductor active layer is provided on an upper surface of the insulator layer, and a transparent source electrode and a transparent drain electrode are disposed partially on the upper surface of the semiconductor active layer and at a distance from each other. This configuration is called a top contact type device. A bottom contact type device in which a source electrode and a drain electrode are disposed under a semiconductor active layer may be also used preferably. In addition, a vertical transistor structure in which a carrier flows in the thickness direction of an organic semiconductor film may be used.

(Active Layer)

Organic semiconductor materials mentioned herein are organic materials showing properties as semiconductors. Examples of the organic semiconductor materials include p-type organic semiconductor materials (or referred to as p-type materials simply or as electron hole transport materials) which conduct electron holes (holes) as carriers, and n-type organic semiconductor materials (or referred to as n-type materials simply or as electrode transport materials) which conduct electrons as carriers, similarly to a semiconductor formed out of an inorganic material. Of the organic semiconductor materials, lots of p-type materials generally show good properties. In addition, p-type transistors are generally excellent in operating stability as transistors under the atmosphere. Here, description here will be made on a p-type organic semiconductor material.

One of properties of organic thin film transistors is a carrier mobility (also referred to as mobility simply) μ which indicates the mobility of a carrier in an organic semiconductor layer. Although preferred mobility varies in accordance with applications, higher mobility is generally preferred. The mobility is preferably not lower than $1.0 \times 10^{-7}$ cm$^2$/Vs, more preferably not lower than $1.0 \times 10^{-6}$ cm$^2$/Vs, further preferably not lower than $1.0 \times 10^{-5}$ cm$^2$/Vs. The mobility can be obtained by properties or TOF (Time Of Flight) measurement when the field effect transistor (FET) device is manufactured.

The p-type organic semiconductor material may be either a low molecular weight material or a high molecular weight material, but preferably a low molecular weight material. Lots of low molecular weight materials typically show excellent properties due to easiness in high purification because various refining processes such as sublimation refining, recrystallization, column chromatography, etc. can be applied thereto, or due to easiness in formation of a highly ordered crystal structure because the low molecular weight materials have a fixed molecular structure. The molecular weight of the low molecular weight material is preferably not lower than 100 and not higher than 5,000, more preferably not lower than 150 and not higher than 3,000, further more preferably not lower than 200 and not higher than 2,000.

As for such a p-type organic semiconductor material, a phthalocyanine compound or a naphthalocyanine compound may be exemplarily used. Specific examples thereof are noted below. Also, M represents a metal atom, Bu represents a butyl group, Pr represents a propyl group, Et represents an ethyl group, and Ph represents a phenyl group.

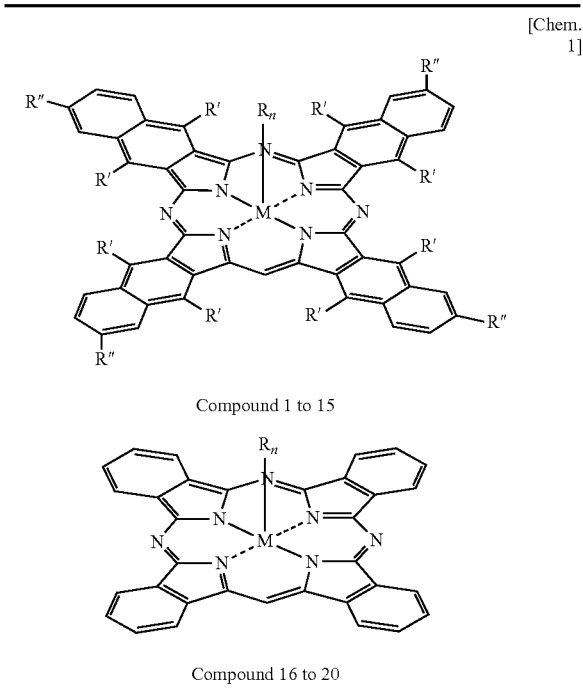

Compound 1 to 15

Compound 16 to 20

| Compound | M | R | n | R' | R'' |
|---|---|---|---|---|---|
| 1 | Si | OSi(n-Bu)$_3$ | 2 | H | H |
| 2 | Si | OSi(i-Pr)$_3$ | 2 | H | H |
| 3 | Si | OSi(OEt)$_3$ | 2 | H | H |
| 4 | Si | OSiPh$_3$ | 2 | H | H |
| 5 | Si | O(n-C$_8$H$_{17}$) | 2 | H | H |
| 7 | Ge | OSi(n-Bu)$_3$ | 2 | H | H |
| 8 | Sn | OSi(n-Bu)$_3$ | 2 | H | H |
| 9 | Al | OSi(n-C$_6$H$_{13}$)$_3$ | 1 | H | H |
| 10 | Ga | OSi(n-C$_6$H$_{13}$)$_3$ | 1 | H | H |
| 11 | Cu | — | — | O(n-Bu) | H |
| 12 | Ni | — | — | O(n-Bu) | H |
| 13 | Zn | — | — | H | t-Bu |
| 14 | V=O | — | — | H | t-Bu |
| 15 | H$_2$ | — | — | H | t-Bu |
| 16 | Si | OSiEt$_3$ | 2 | — | — |
| 17 | Ge | OSiEt$_3$ | 2 | — | — |
| 18 | S | OSiEt$_3$ | 2 | — | — |
| 19 | Al | OSiEt$_3$ | 1 | — | — |
| 20 | Ga | OSiEt$_3$ | 1 | — | — |

(Switching Element Constituent Components Other than the Active Layer)

There is no particular limitation in the material constituting the gate electrode, the source electrode, or the drain electrode, as long as it has a required conductivity. However, examples thereof may include a transparent conductive oxide such as ITO (indium-doped tin oxide), IZO (indium-doped zinc oxide), SnO$_2$, ATO (antimony-doped tin oxide), ZnO, AZO (aluminum-doped zinc oxide), GZO (gallium-doped zinc oxide), TiO$_2$, or FTO (fluorine-doped tin oxide), a transparent conductive polymer such as PEDOT/PSS([poly(3,4-ethylenedioxythiophene)/polystyrene sulfonic acid), or a carbon material such as carbon nanotube. These electrode materials may be film-formed by, for example, a vacuum evaporation method, a sputtering method, or a solution coating method.

There is no particular limitation in the material used for the insulating layer, as long as it has a required insulating effect. Examples thereof may include an inorganic material such as silicon dioxide, silicon nitride, or alumina, or an organic material such as polyester (e.g., PEN (polyethylene naphthalate), PET (polyethylene terephthalate)), polycarbonate, polyimide, polyamide, polyacrylate, epoxy resin, poly-para-xylylene resin, novolac resin, PVA (polyvinyl alcohol), PS (polystyrene). These insulating film materials may be film-formed by, for example, a vacuum evaporation method, a sputtering method, or a solution coating method.

Other configurations on the above described organic TFT may refer to the description of Japanese Patent Application Laid-Open No 2009-212389.

Also, in the active layer of the switching elements 28, for example, an amorphous oxide described in Japanese Patent Application Laid-Open No 2010-186860 may be used. Hereinafter, an active layer containing the amorphous oxide included in a field effect transistor (FET) described in Japanese Patent Application Laid-Open No 2010-186860 will be described. The active layer serves as a channel layer of the FET, allowing electrons or holes to move.

The active layer is configured to include an amorphous oxide semiconductor. The amorphous oxide semiconductor may be film-formed at a low temperature, and thus may be appropriately formed on a flexible substrate. The amorphous oxide semiconductor used in the active layer may be preferably an amorphous oxide that includes at least one kind element selected from the group including In, Sn, Zn, and Cd, more preferably an amorphous oxide that includes at least one kind selected from the group including In, Sn, and Zn, and further more preferably, an amorphous oxide that includes at least one kind selected from the group including In, and Zn.

Examples of the amorphous oxide used in the active layer, specifically, may include In$_2$O$_3$, ZnO, SnO$_2$, CdO, Indium-Zinc-Oxide (IZO), Indium-Tin-Oxide (ITO), Gallium-Zinc-Oxide (GZO), Indium-Gallium-Oxide (IGO), or Indium-Gallium-Zinc-Oxide (IGZO).

As for the film forming method of the active layer, a vapor-phase film formation method may be preferably used with a polycrystalline sintered body of the oxide semiconductor as a target. Among vapor-phase film formation methods, a sputtering method, or a pulsed laser deposition method (PLD method) is suitable. Further, from the view point of mass production, the sputtering method is preferable. For example, the film formation may be performed by an RF magnetron sputtering evaporation method while the degree of vacuum and the oxygen flow rate are controlled.

The film-formed active layer is determined to be an amorphous film, through a known X-ray diffraction method. The composition ratio of the active layer may be obtained by an RBS (Rutherford Back Scattering) analysis method.

Further, the electrical conductivity of the active layer is preferably $10^{-4}$ Scm$^{-1}$ or more and less than $10^2$ Scm$^{-1}$, and more preferably $10^{-1}$ Scm$^{-1}$ or more and less than $10^2$ Scm$^{-1}$. A method of adjusting the electrical conductivity of the active layer may include known methods such as an adjustment method according to oxygen defects, an adjustment method according to a composition ratio, an adjustment method according to impurities, and an adjustment method according to an oxide semiconductor material.

Other configurations on the above amorphous oxide may refer to the description of Japanese Patent Application Laid-Open No 2010-186860.

[Insulating Substrate]

The substrate is not limited particularly as long as it has required smoothness. Examples of the substrate include glass, quartz, light transmissive plastic film, etc. Examples of the light transmissive plastic film include films or the like, made from polyethylene terephthalate (PET), polyethylene naphthalate (PEN), polyether sulfone (PES), polyether imide, polyetheretherketone, polyphenylene sulfide, polyalylate, polyimide, polycarbonate (PC), cellulose triacetate (TAC), cellulose acetate propionate (CAP), etc. In addition, any organic or inorganic filler may be contained in these plastic films. It may be considered that aramid, bionanofiber, etc. having properties such as flexibility, low thermal expansion and high strength, which cannot be obtained in existing glass or plastic, are used preferably to form a flexible substrate.

(Aramid)

An aramid material has high heat resistance showing a glass transition temperature of 315° C., high rigidity showing a Young's modulus of 10 GPa, and high dimensional stability showing a thermal expansion coefficient of −3 to 5 ppm/° C. Therefore, when a film made from aramid is used, it is possible to easily form a high-quality film for a semiconductor layer, as compared with the case where a general resin film is used. In addition, due to the high heat resistance of the aramid material, an electrode material can be cured at a high temperature to have low resistance. Further, it is also possible to deal with automatic mounting with ICs, including a solder reflow step. Furthermore, since the aramid material has a thermal expansion coefficient close to that of ITO (indium tin oxide), a gas barrier film or a glass substrate, warp after manufacturing is small. In addition, cracking hardly occurs. Here, it is preferable to use a halogen-free (in conformity with the requirements of JPCA-ES01-2003) aramid material containing no halogens, in view of reduction of environmental load.

The aramid film may be laminated with a glass substrate or a PET substrate, or may be pasted onto a housing of a device.

High intermolecular cohesion (hydrogen bonding force) of aramid leads to low solubility to a solvent. When the problem of the low solubility is solved by molecular design, an aramid material easily formed into a colorless and transparent thin film can be used preferably. Due to molecular design for controlling the order of monomer units and the substituent species and position on an aromatic ring, easy formation with good solubility can be obtained with the molecular structure kept in a bar-like shape with high linearity leading to high rigidity or dimensional stability of the aramid material. Due to the molecular design, halogen-free can be also achieved.

In addition, an aramid material having an optimized characteristic in an in-plane direction of a film can be used preferably. Tensional conditions are controlled in each step of solution casting, vertical drawing and horizontal drawing in accordance with the strength of the aramid film which varies constantly during casting. Due to the control of the tensional conditions, the in-plane characteristic of the aramid film which has a bar-like molecular structure with high linearity leading to easy occurrence of anisotropic physicality can be balanced.

Specifically, in the solution casting step, the drying rate of the solvent is controlled to make the in-plane thickness-direction physicality isotropic and optimize the strength of the film including the solvent and the peel strength from a casting drum. In the vertical drawing step, the drawing conditions are controlled precisely in accordance with the film strength varying constantly during drawing and the residual amount of the solvent. In the horizontal drawing, the horizontal drawing conditions are controlled in accordance with a change in film strength varying due to heating and controlled to relax the residual stress of the film. By use of such an aramid material, the problem that the aramid film after casting may be curled.

In each of the contrivance for the easiness of casting and the contrivance for the balance of the film in-plane characteristic, the bar-like molecular structure with high linearity peculiar to aramid can be kept to keep the thermal expansion coefficient low. When the drawing conditions during film formation are changed, the thermal expansion coefficient can be reduced further.

(Bio-Nanofiber)

Components sufficiently small relative to the wavelength of light produce no scattering of the light. Accordingly, nanofibers may be used as a support for a transparent flexible resin material. And, of the nanofibers, a composite material (occasionally referred to as bionanofiber) of bacterial cellulose and transparent resin can be used preferably. The bacterial cellulose is produced by bacteria (*Acetobacter Xylinum*). The bacterial cellulose has a cellulose microfibril bundle width of 50 nm, which is about 1/10 as large as the wavelength of visible light. In addition, the bacterial cellulose is characterized by high strength, high elasticity and low thermal expansion.

When a bacterial cellulose sheet is impregnated with transparent resin such as acrylic resin or epoxy resin and hardened, transparent bionanofiber showing a light transmittance of about 90% in a wavelength of 500 nm while having a high fiber ratio of about 60 to 70% can be obtained. By the bionanofiber, a thermal expansion coefficient (about 3 to 7 ppm) as low as that of silicon crystal, strength (about 460 MPa) as high as that of steel, and high elasticity (about 30 GPa) can be obtained.

As for the configuration about the aforementioned bio-nanofiber, for example, refer to description in JP-A-2008-34556.

[Flattening Layer and Adhesive Layer]

There is no specific limitation in the flattening layer 23 and the adhesive layer 25 as the resin layer which allows the scintillator 18 and the photoelectric conversion elements 26 to be optically coupled, as long as it may allow the fluorescence of the scintillator 18 to reach the photoelectric conversion elements 26 without attenuation. As the flattening layer 23, a resin such as polyimide or parylene may be used, and polyimide with a good film-forming property is preferred. As for the adhesive layer 25, for example, a thermoplastic resin, a UV-curable adhesive, a heat curing adhesive, a room temperature setting adhesive, a double-sided adhesive sheet may be used. However, from the viewpoint of not degrading the sharpness of an image, it is preferable to use an adhesive made of a low viscosity epoxy resin since it may form a sufficiently thin adhesive layer with respect to an element size.

Hereinafter, specific examples of manufacturing the radiological image detection apparatus will be described, but the present invention is not limited to these Manufacturing Examples.

Manufacturing Example 1

1. Manufacturing of a Radiological Image Conversion Panel

As the support 11, an alkali-free glass substrate for liquid crystals (0.7 mm thickness) was prepared. First, the support 11 was surface-treated with Ar plasma so as to improve the adhesion with the scintillator. Then, the surface-treated support was set in a vacuum chamber for film formation of the scintillator. The vacuum chamber is provided with a plurality of crucibles so as to independently heat each of CsI and Tl of a raw material. After the chamber was exhausted, the degree of vacuum of a device was set as 0.75 Pa by inflow of Ar in a predetermined amount. At the point of time when the melt state of the raw material was stabilized by heating the raw material crucible, the support was concentrically rotated by a device mechanism of the vacuum device. The shutter was opened to start the vapor deposition of the non-columnar section 36.

Under this condition, film preparation was performed. At the point of time when the thickness t2 of the non-columnar section 36 became 5 μm, the degree of vacuum was increased to 1 Pa to start the vapor deposition of the columnar section 34. When the degree of vacuum is varied, the melt state of the raw material is varied. Thus, before the vapor deposition was resumed, the shutter was closed. Then, when the melt state was determined to be stabilized, the shutter was opened again. At the point of time when the thickness t1 of the columnar section 34 became 500 μm, the heating of the raw material crucible was stopped. Through vapor deposition on the support by inhalation of the vacuum device, the scintillator 18 including the non-columnar section 36 and the columnar section 34 was formed.

2. Test on Properties of Scintillator 2-1. Measurement on Thickness t2 of Non-Columnar Section and Thickness t1 of Columnar Section Any part of the scintillator 18 was fractured, and was observed in the growth direction of columnar crystals by SEM so as to measure the film thicknesses of the columnar section 34 and the non-columnar section 36. As the film thickness value, an average value of values measured at 10 locations randomly selected at the extracted part was used. Also, the SEM observation was performed after sputtering of Au to about 200 Å because CsI has non-conductivity.

2-2. Measurement of Crystal Diameter

A part of the scintillator 18 was peeled off from the support 11, and was observed in the plane perpendicular to the growth direction of the columnar crystals by SEM so as to measure the columnar diameter (cross-sectional diameter of the columnar crystals). Observation was performed with a magnification (about 2,000×) that allows 100 to 200 columnar crystals to be observed when the scintillator was viewed from the surface at one shot. Then, a value obtained by measuring and taking an average on the maximum values of the crystal diameters obtained for all the crystals included at the one shot is employed. Also, in a case where crystals are bonded to each other like in the non-columnar section 36, a line connecting concave portions (recesses) occurring between the adjacent crystals was considered as a grain boundary between the crystals, and the bonded crystals were separated to be the smallest polygons so as to measure a crystal diameter. The crystal diameters (μm) were read to two decimal places, and the average value was determined by rounding off to one decimal place in accordance with JIS Z 8401.

When it is difficult to peel off the scintillator 18 from the support 11, the scintillator 18 was vertically sliced in the growth direction of the columnar crystals at a position of about 100 um from the support 11. Then etching of Ar ions was performed up to a distance allowing the interfacial shape of CsI crystals attached on the support 11 to be observed, and then observation was performed from the etching plane. Since CsI is non-conductive, SEM observation was performed after sputtering Au to about 20 Å.

3. Manufacturing of Radiological Image Detection Apparatus

The sensor panel 3 was prepared, and on the surface thereof, a low viscosity epoxy resin adhesive (manufactured by HUNTSMAN Corp, Araldite 2020) diluted with a solvent was applied through spin-coating so that the thickness after solvent evaporation may be 15 μm. Then, the adhesive layer 25 was formed. After the adhesive layer 25 formed on the sensor panel 3 face the columnar section 34 side of the scintillator 18, the radiological image conversion panel 2 was bonded to the sensor panel 3 via the adhesive layer 25 through heating.

Then, on a terminal unit of the sensor panel 3, a circuit board for driving a TFT, and an integrated circuit IC for reading out electric charges were adhered by an anisotropic conductive film, which was connected to a circuit board designed for control driving and AD conversion so as to provide the radiological image detection apparatus of Manufacturing Example 1.

Radiation was disposed to be incident from the sensor panel 3 side, and a radiological image was read out by controlling a PC for scanning connected to the radiological image detection apparatus 1 via a cable.

Manufacturing Examples 2 to 6

Radiological image detection apparatus in Manufacturing Example 2 to 6 were manufactured in the same manner as described in Manufacturing Example 1 except that the film thickness of the non-columnar section 36 was adjusted as noted in Table 1 by changing the vapor deposition time at the time of degree of vacuum of 0.75 Pa.

Manufacturing Examples 7 to 11

Radiological image detection apparatus in Manufacturing Example 7 to 11 were manufactured in the same manner as described in Manufacturing Example 1 except that in the film formation of the non-columnar section 36, the degree of vacuum was changed as noted in Table 1, and the crystal diameter in the non-columnar section 36 was adjusted as noted in Table 1.

Manufacturing Example 12

As a support, in place of the glass substrate used in Manufacturing Example 1, a glass substrate which has a surface formed with an unevenness at a height of about 5 μm with 5 μm pitch through wet etching was used. Then, a radiological image detection apparatus in Manufacturing Example 12 was manufactured in the same manner as described in Manufacturing Example 1 except that in the formation of the scintillator 18, the columnar section was directly vapor-deposited on the support without vapor deposition of the non-columnar section.

Manufacturing Example 13

The scintillator 18 was directly film-formed on the surface of the sensor panel 3 instead of the glass substrate used as a support in Manufacturing Example 3 in the same condition of Manufacturing Example 3. In the present embodiment, in the vicinity of the sensor panel 3, the non-columnar section 36 is first formed, and then, the columnar section 34 is formed, but bonding through a thermosetting adhesive is not performed.

Others than this processing were performed in the same manner as described in Manufacturing Example 3.

4. Test on Properties of Radiological Image Detection Apparatus

4-1. Sensitivity

As radiation, X-rays were used. At the irradiation of the X-rays, the sensor panel 3 was driven by an electrical circuit so as to read out electric charges generated in each of the photoelectric conversion elements 26 by scintillation light. Then, the quantity of the generated electric charges was calculated by AD conversion after amplification through a electric charge amplifier.

The quantity of electric charges (noise of a detection system) read out at non-irradiation of the X-rays was previously measured, and a value obtained by subtracting this quantity from the quantity of electric charges generated at the irradiation of the X-rays was set as sensitivity. The result is noted in Table 1. Also, this value is indicated by a relative value with respect to 100 of sensitivity in Manufacturing Example 12.

4-2. MTF (Modulation Transfer Function)

In accordance with IEC standards, an edge image obtained by photographing an MTF edge made of W (tungsten) was computed so as to obtain an MTF curve. The result is noted in Table 1. Also, as compared to the value of 2 cycle/mm, this value is indicated by a relative value with respect to 100 of the value in Manufacturing Example 12.

4-3. Overall Determination

The product of the test results of the sensitivity and the MTF was used as indicator so as to determine the performance of the radiological image detection apparatus. The product of the sensitivity and the MTF is preferably 120 or more because a difference in performance may be significantly recognized in a sensory evaluation of an image.

TABLE 1

| | Phosphor Film Forming Method | | Phosphor Shape | | | | | | Evaluation result | | |
|---|---|---|---|---|---|---|---|---|---|---|---|
| | | Degree of vacuum | | Non-columnar diameter | | | Columnar diameter | | Film | | | Overall |
| | Support | Non-columnar section | Columnar section | Film thickness t2 | Mean crystal diameter | Porosity (%) | Film thickness t1 | Mean columnar diameter | thickness ratio t2/t1 | Sensitivity | MTF | Determination |
| Manufacturing Example 1 | Alkali-free glass | 0.75 Pa | 1 Pa | 5 | 3.3 | 9.0 | 500 | 7.6 | 0.01 | 120 | 100 | 120 |
| Manufacturing Example 2 | Alkali-free glass | 0.75 Pa | 1 Pa | 10 | 3.0 | 9.2 | 500 | 7.2 | 0.02 | 121 | 100 | 121 |
| Manufacturing Example 3 | Alkali-free glass | 0.75 Pa | 1 Pa | 25 | 3.0 | 9.0 | 500 | 6.8 | 0.05 | 123 | 101 | 124 |
| Manufacturing Example 4 | Alkali-free glass | 0.75 Pa | 1 Pa | 50 | 3.1 | 9.1 | 500 | 7.2 | 0.10 | 122 | 100 | 122 |
| Manufacturing Example 5 | Alkali-free glass | 0.75 Pa | 1 Pa | 125 | 3.4 | 9.3 | 500 | 7.1 | 0.25 | 120 | 100 | 120 |
| Manufacturing Example 6 | Alkali-free glass | 0.75 Pa | 1 Pa | 170 | 3.2 | 9.3 | 500 | 7.0 | 0.34 | 121 | 94 | 114 |
| Manufacturing Example 7 | Alkali-free glass | 0.1 Pa | 1 Pa | 25 | 11.2 | 4.0 | 500 | 6.8 | 0.05 | 111 | 91 | 101 |
| Manufacturing Example 8 | Alkali-free glass | 0.3 Pa | 1 Pa | 25 | 8.0 | 7.0 | 500 | 7.0 | 0.05 | 117 | 99 | 116 |
| Manufacturing Example 9 | Alkali-free glass | 0.5 Pa | 1 Pa | 25 | 6.2 | 8.8 | 500 | 7.0 | 0.05 | 123 | 100 | 123 |
| Manufacturing Example 10 | Alkali-free glass | 1.5 Pa | 1 Pa | 25 | 1.5 | 9.4 | 500 | 7.2 | 0.05 | 122 | 100 | 122 |
| Manufacturing Example 11 | Alkali-free glass | 3 Pa | 1 Pa | 25 | 0.5 | 9.3 | 500 | 7.0 | 0.05 | 122 | 100 | 122 |
| Manufacturing Example 12 | Patterning substrate | — | 1 Pa | — | — | — | 500 | 6.8 | — | 100 | 100 | 100 |
| Manufacturing Example 13 | Photo-detector (TFT) substrate | 0.75 Pa | 1 Pa | 25 | 3.1 | 9.0 | 500 | 6.9 | 0.05 | 98 | 96 | 94 |

As clearly noted in Table 1, it can be seen that as compared to the radiological image detection apparatus having the scintillator 18 including only the columnar section 34 in Manufacturing Example 12, the radiological image detection apparatus in Manufacturing Examples 1 to 11 have a higher sensitivity and also may suppress image deterioration such as image blur so as to achieve a high sharpness of an obtained image.

Also, through Manufacturing Examples 1 to 11, it can be seen that when the ratio t2/t1 of the thickness t2 of the non-columnar section 36 to the thickness t1 of the columnar section 34 is within a preferred range, and the crystal diameter of the non-columnar section 36 is within a preferred range, it is possible to especially achieve a good sensitivity, and to suppress image blur.

As described above, the present description discloses a radiological image conversion panel provided with a phosphor containing a fluorescent material that emits fluorescence by radiation exposure, in which the phosphor comprises, a columnar section formed by a group of columnar crystals which are obtained through columnar growth of crystals of a fluorescent material, and a non-columnar section, the columnar section and the non-columnar section are integrally formed to overlap in a crystal growth direction of the columnar crystals, and a thickness of the non-columnar section along the crystal growth direction is non-uniform in a region of at least a part of the non-columnar section.

And, in the radiological image conversion panel disclosed in the present description, a difference between a maximum thickness and a minimum thickness in a central region of the non-columnar section is less than a difference between a maximum thickness and a minimum thickness in a peripheral region of the non-columnar section.

And, in the radiological image conversion panel disclosed in the present description, a deviation in a thickness distribution in a central region of the non-columnar section is less than a deviation in a thickness distribution in a peripheral region of the non-columnar section.

And, in the radiological image conversion panel disclosed in the present description, the thickness of the non-columnar section is non-uniform only in the peripheral region.

And, in the radiological image conversion panel disclosed in the present description, the thickness of the non-columnar section is distributed within a range of 5 μm or more and 125 μm or less.

And, in the radiological image conversion panel disclosed in the present description, the non-columnar section is formed while comprising a group of spherical crystals obtained by growing crystals of the fluorescent material in a substantial spherical shape, in which at least a part of the group of the spherical crystals is fused in an in-plane direction.

And, the present description discloses a method of manufacturing the aforementioned radiological image conversion panel, in which the non-columnar section and the columnar section are formed in this order on a support by depositing crystals of the fluorescent material on the support by a vapor deposition method, in which when the non-columnar section is formed, the crystals of the fluorescent material are deposited on the support by varying a degree of vacuum.

And, the present description discloses a radiological image detection apparatus provided with the aforementioned radiological image conversion panel, and a sensor panel which detects fluorescence generated from the radiological image conversion panel and converts the fluorescence into an electrical signal.

And, in the radiological image detection apparatus disclosed in the present description, the radiological image conversion panel and the sensor panel are bonded to each other so that a surface of the columnar section side of the phosphor faces the sensor panel.

And, the radiological image detection apparatus disclosed in the present description has a radiation entrance surface at the sensor panel side.

And, the radiological image detection apparatus disclosed in the present description has a radiation entrance surface at the radiological image conversion panel side.

The present invention has been described in detail with reference to specific exemplary embodiments. However, it is apparent to those skilled in the art that various changes and modification may be made without departing from the spirit and scope of the present invention. The present application is based on Japanese Patent Application No. 2010-291390 filed 27 Dec. 2010, and the contents thereof are incorporated herein by reference.

INDUSTRIAL APPLICABILITY

The present invention may detect a radiological image with a high sensitivity and a high definition, and thus may be used while embedded within various devices requiring detection of a sharp image at a low radiation irradiation dose, including an X-ray imaging device for medical diagnosis such as mammography. For example, the device has a wide application range because it may be used as an X-ray imaging device for industrial use for a non-destructive test, or as a device for detecting corpuscular beams (α rays, β-rays, γ rays) besides electromagnetic waves.

REFERENCE SIGNS LIST

1: radiological image detection apparatus
2: radiological image conversion panel
3: sensor panel
11: support
16: TFT substrate
18: scintillator
20: photoconductive layer
22: electrode
23: flattening layer
24: electrode
25: adhesive layer
26: photoelectric conversion elements
28; switching element
30: gate lines
32: signal line
34: columnar section
36: non-columnar section
38: connection terminal

The invention claimed is:
1. A radiological image conversion panel provided with a phosphor containing a fluorescent material that emits fluorescence by radiation exposure,
   wherein the phosphor comprises a columnar section formed by a group of columnar crystals which are obtained through columnar growth of crystals of a fluorescent material, and a non-columnar section,
   the columnar section and the non-columnar section are integrally formed on a support to overlap in a crystal growth direction of the columnar crystals in an order of the non-columnar section and the columnar section,
   the thickness of the non-columnar section along the crystal growth direction is non-uniform throughout the non-columnar section, the difference between the maximum thickness and the minimum thickness in the central region of the non-columnar section is less than the difference between the maximum thickness and the minimum thickness in the peripheral region of the non-columnar section, a diameter of each crystal constituting the non-columnar section is 0.5 μm or more and 7.0 μm or less, the crystals of the non-columnar section irregularly overlap, and some crystals thereof are fused to each other in a thickness direction or an in-plane direction, and the non-columnar section includes a non-crystalline part.

2. The radiological image conversion panel of claim 1, wherein the thickness of the non-columnar section is distributed within a range of 5 μm or more and 125 μm or less.

3. The radiological image conversion panel of claim 1, wherein the non-columnar section is formed while comprising a group of spherical crystals obtained by growing crystals of the fluorescent material in a substantial spherical shape, wherein at least a part of the group of the spherical crystals is fused in a direction parallel to a surface of the support.

4. A method of manufacturing the radiological image conversion panel of claim 1, wherein the non-columnar section and the columnar section are formed in this order on the support by depositing crystals of the fluorescent material on the support by a vapor deposition method, wherein when the non-columnar section is formed, the crystals of the fluorescent material are deposited on the support by varying a degree of vacuum.

5. A radiological image detection apparatus provided with the radiological image conversion panel of claim 1, and a sensor panel which detects fluorescence generated from the radiological image conversion panel and converts the fluorescence into an electrical signal.

6. The radiological image detection apparatus of claim 5, wherein the radiological image conversion panel and the sensor panel are bonded to each other so that a surface of the columnar section side of the phosphor faces the sensor panel.

7. The radiological image detection apparatus of claim 6, which has a radiation entrance surface at the sensor panel side.

8. The radiological image detection apparatus of claim 6, which has a radiation entrance surface at the radiological image conversion panel side.

9. A radiological image conversion panel provided with a phosphor containing a fluorescent material that emits fluorescence by radiation exposure, wherein the phosphor comprises a columnar section formed by a group of columnar crystals which are obtained through columnar growth of crystals of a fluorescent materials, and a non-columnar section, the columnar section and the non-columnar section are integrally formed on a support to overlap in a crystal growth direction of the columnar crystals in an order of the non-columnar section and the columnar section, the thickness of the non-columnar section along the crystal growth direction is non-uniform throughout the non-columnar section, the deviation in the thickness distribution in the central region of the non-columnar section is less than the deviation in the thickness distribution in the peripheral region of the non-columnar section, a diameter of each crystal constituting the non-columnar section is 0.5 μm or more and 7.0 μm or less, the crystals of the non-columnar section irregularly overlap, and some crystals thereof are fused to each other in a thickness direction or an in-plane direction, and the non-columnar section includes a non-crystalline part.

10. The radiological image conversion panel of claim 9, wherein the thickness of the non-columnar section is distributed within a range of 5 μm or more and 125 μm or less.

11. The radiological image conversion panel of claim 9, wherein the non-columnar section is formed while comprising a group of spherical crystals obtained by growing crystals of the fluorescent material in a substantial spherical shape, wherein at least a part of the group of the spherical crystals is fused in a direction parallel to a surface of the support.

12. A method of manufacturing the radiological image conversion panel of claim 9, wherein:

the non-columnar section and the columnar section are formed in this order on the support by depositing crystals of the fluorescent material on the support by a vapor deposition method, and when the non-columnar section is formed, the crystals of the fluorescent material are deposited on the support by varying a degree of vacuum.

13. A radiological image detection apparatus provided with the radiological image conversion panel of claim 9, and a sensor panel which detects fluorescence generated from the radiological image conversion panel and converts the fluorescence into an electrical signal.

14. The radiological image detection apparatus of claim 13, wherein the radiological image conversion panel and the sensor panel are bonded to each other so that a surface of the columnar section side of the phosphor faces the sensor panel.

15. The radiological image detection apparatus of claim 14, which has a radiation entrance surface at the sensor panel side.

16. The radiological image detection apparatus of claim 14, which has a radiation entrance surface at the radiological image conversion panel side.

* * * * *